(12) United States Patent
Bucciotti et al.

(10) Patent No.: US 9,931,301 B2
(45) Date of Patent: Apr. 3, 2018

(54) METHOD FOR THE REALISATION OF A BIOMATERIAL COMPRISING CALCIUM PHOSPHATE SHAPED AS GRANULES AND/OR THEIR AGGLOMERATES AND BIOMATERIAL OBTAINED WITH THIS METHOD

(75) Inventors: Francesco Bucciotti, Civezzano (IT); Marzio Piccinini, Lavarone (IT); Vincenzo Maria Sglavo, Roncegno Terme (IT)

(73) Assignee: EUROCOATING S.P.A., Pergine Valsugana (Trento) (IT)

( * ) Notice: Subject to any disclaimer, the term of this patent is extended or adjusted under 35 U.S.C. 154(b) by 0 days.

(21) Appl. No.: 14/110,073

(22) PCT Filed: Apr. 5, 2012

(86) PCT No.: PCT/IB2012/051709
§ 371 (c)(1),
(2), (4) Date: Nov. 18, 2013

(87) PCT Pub. No.: WO2012/137174
PCT Pub. Date: Oct. 11, 2012

(65) Prior Publication Data
US 2014/0072641 A1  Mar. 13, 2014

(30) Foreign Application Priority Data
Apr. 6, 2011 (IT) .............................. VR2011A0069

(51) Int. Cl.
| | | |
|---|---|---|
| *A61K 9/16* | (2006.01) | |
| *A61L 27/12* | (2006.01) | |
| *A61L 27/46* | (2006.01) | |
| *A61L 27/56* | (2006.01) | |
| *A61L 27/42* | (2006.01) | |

(52) U.S. Cl.
CPC .......... *A61K 9/1611* (2013.01); *A61K 9/1682* (2013.01); *A61L 27/12* (2013.01); *A61L 27/425* (2013.01); *A61L 27/46* (2013.01); *A61L 27/56* (2013.01)

(58) Field of Classification Search
CPC .......... A61L 27/12; A61L 27/46; A61L 27/56; A61K 9/1611; A61K 9/1682; C08L 5/08; C08L 5/04
See application file for complete search history.

(56) References Cited

U.S. PATENT DOCUMENTS

| 7,326,464 B2 | 2/2008 | Lemaitre et al. | |
| 2007/0269505 A1* | 11/2007 | Flath et al. | ................... 424/451 |
| 2009/0005881 A1* | 1/2009 | Kamitakahara et al. | .. 623/23.61 |
| 2011/0008460 A1* | 1/2011 | Riman et al. | ................. 424/602 |

FOREIGN PATENT DOCUMENTS

| CN | 101401958 | 4/2009 |
| JP | H02180709 | 7/1990 |
| WO | WO0181243 | 11/2001 |
| WO | WO2005082780 | 9/2005 |
| WO | WO2008041774 | 4/2008 |

OTHER PUBLICATIONS

Xiangnan Li, et al.. "Synthesis and Characterization of Core-Shell Hydroxyapatite/Chitosan Biocomposite Nanospheres". Journal of Wuhan University of Technology-Mater. Sci. Ed, Apr. 2010, pp. 252-256, vol. 25, No. 2.

* cited by examiner

*Primary Examiner* — Jessica Worsham
(74) *Attorney, Agent, or Firm* — Tutujian & Bitetto, P.C.

(57) ABSTRACT

Method for the realization Hof a calcium phosphate-based biomaterial in form of granules and/or agglomerates of re-absorbable granules which can be used in the biomedical industry as, e.g., bone fillers, for increasing the bone mass, as a sealing for the internal orthopaedic prosthesis, for releasing drugs and/or medicaments and/or other substances beneficial for the organism. A calcium phosphate-based biomaterial in form of granules and/or aggregates thereof obtained according to such method.

26 Claims, 4 Drawing Sheets

METHOD FOR THE REALISATION OF A BIOMATERIAL COMPRISING CALCIUM PHOSPHATE SHAPED AS GRANULES AND/OR THEIR AGGLOMERATES AND BIOMATERIAL OBTAINED WITH THIS METHOD

TECHNICAL FIELD OF THE INVENTION

The present invention regards a method for providing a calcium phosphate-based biomaterial in form of granules and/or aggregates thereof which can be used in the biomedical industry as bone fillers, for increasing the bone mass, as a sealing for the internal orthopaedic prosthesis, for releasing drugs and/or medicaments and/or other substances beneficial for the organism, etcetera.

The present invention further regards the calcium phosphate-based biomaterial in form of granules and/or aggregates thereof obtained according to such method.

DESCRIPTION OF RELATED ART

In the biomaterial industry, in particular of re-absorbable biomaterial useable in the biomedical industry, especially in the orthopaedic and surgical industry, ceramic and/or polymeric biomaterials are mostly currently used substantially for fixing prosthesis or as bone substitutes, for filling cavities or lacunae of various types or origin.

The use of calcium phosphate-based ceramic materials in bone regeneration, in form of injectable microparticles, has been considerably popular over the last years due to the good biological responses obtained from such materials and the suitable mechanical properties thereof.

Furthermore, calcium phosphate-based compounds are known and used in biomedical applications due to the chemical composition thereof similar to the mineral inorganic fraction of the bone tissue, a characteristic that makes them biocompatible, bioactive and osteoconductive, in the sense that they stimulate bone regeneration and molecular ionic exchange with the tissue.

For example, U.S. Pat. No. 7,326,464 describes porous calcium phosphate microgranules starting from a hydroxyapatite and beta-tricalcium phosphate powder to which organic or inorganic additives such as de-flocculants, plasticizers, bonding agents, porogen agents, and etcetera, alongside various types of jellifying agents are added.

However, such materials reveal some drawbacks, lying in the fact that methods used for the provision thereof are very complex and laborious; the porosity is obtained due to the addition of porogen agents and it is not inherent in the very process; furthermore, some parameters or solutions used do not fully meet the needs required by the specific sector.

Furthermore, the use and incineration of polymeric porogens, such as polyacrylic acid (PAA), may produce a harmful carbonaceous solid residue which may remain in the granule at the end of sinterization. Furthermore, the uncontrolled use of organic products may result in a phase transformation of the initial powder during the heat treatment and thus obtaining a composition of the microgranules different from the desired one.

SUMMARY OF THE INVENTION

The technical task of the present invention is thus that of improving the state of the art.

Providing a method for obtaining a calcium phosphate-based biomaterial in form of granules and/or aggregates thereof made of biocompatible material suitable to be interfaced with organic tissues without generating adverse reactions in the tissue or at systemic level represents an object of the invention within this technical field.

A further object of the present invention is that of providing a method for obtaining a calcium phosphate-based biomaterial in form of granules and/or aggregates thereof made of material that is biocompatible, porous and re-absorbable in the tissue with which it is interfaced and usable in the bone regeneration industry, as a bone filler and for releasing drugs or other substances, etcetera.

A further object of the present invention is to provide a method that is simple to obtain, with the possibility of using materials currently available in the market.

Still another object of the present invention is to provide a method that is inexpensive and easily repeatable.

These and other objects are attained by a method for providing a calcium phosphate-based biomaterial in form of granules and aggregates thereof made of biocompatible material according to aspects of the present invention.

Providing a calcium phosphate-based biomaterial in form of granules and/or aggregates of granules made of biocompatible material suitable for being interfaced with organic tissues without creating adverse reactions in the tissue or at systemic level constitutes an object of the present invention within the technical field of the invention.

A further object of the present invention is to provide a calcium phosphate-based biomaterial in form of granules and/or aggregates of granules made of biocompatible material that is porous and re-absorbable in the tissue with which it is interfaced and useable in the bone regeneration industry, as a bone filler and for releasing drugs or other substances, etcetera.

Still, a further object of the invention is to provide a calcium phosphate-based biomaterial in form of granules and/or aggregates of granules that are simple to obtain, with the possibility of using materials currently available in the market.

A further object of the present invention is to provide a calcium phosphate-based biomaterial in form of granules and/or aggregates of granules that are inexpensive and that have highly reproducible characteristics.

These and other objects are attained by a calcium phosphate-based biomaterial in form of granules and/or aggregates of granules according to aspects of the present invention.

In one aspect, a method for the realization of a calcium phosphate-based biomaterial in form of granules and/or agglomerates of re-absorbable granules is provided comprising the steps of providing at least one calcium phosphate-based ceramic powder, providing at least one aqueous solution comprising a natural polysaccharide dissolved in said aqueous solution, preparing at least one ceramic suspension obtained by mixing said ceramic powder in said aqueous solution, extruding the at least one ceramic suspension in a laminar flow, fragmenting the laminar flow of the at least one ceramic suspension into droplets by means of physical methods or through any other technology suitable for the purpose, immersing—by dropping—the droplets of ceramic solution into a cross-linking solution, maintaining the droplets in the cross-linking solution with ensuing consolidation and jellification of the droplets which assume a conformation of particles, washing the particles in water or any other liquid suitable for eliminating the excess of material and possible impurities, drying the particles through manual or automated separation thereof, so as to avoid the contact thereof, obtaining granules and/or agglomerates with automated or manual compaction of the particles, obtaining agglomerates of granules, wherein in the drying step a microporosity is formed made up by pores of micrometric dimensions and/or a macroporosity between one granule and another of the agglomerates.

BRIEF DESCRIPTION OF THE DRAWINGS

These and other advantages shall be clearer to those skilled in the art from the description that follows and from the attached drawings, provided by way of non-limiting examples, wherein.

DETAILED DESCRIPTION OF PREFERRED EMBODIMENTS

Figure 1:
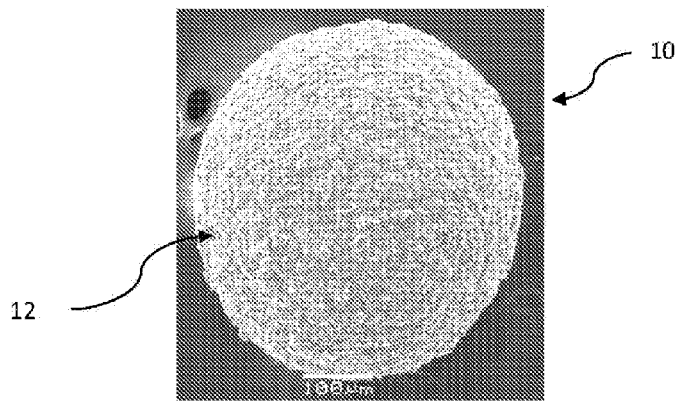
FIG. 1 illustrates an image obtained from the scanning electron microscope (SEM) of a granule according to the present invention.
Figure 2:
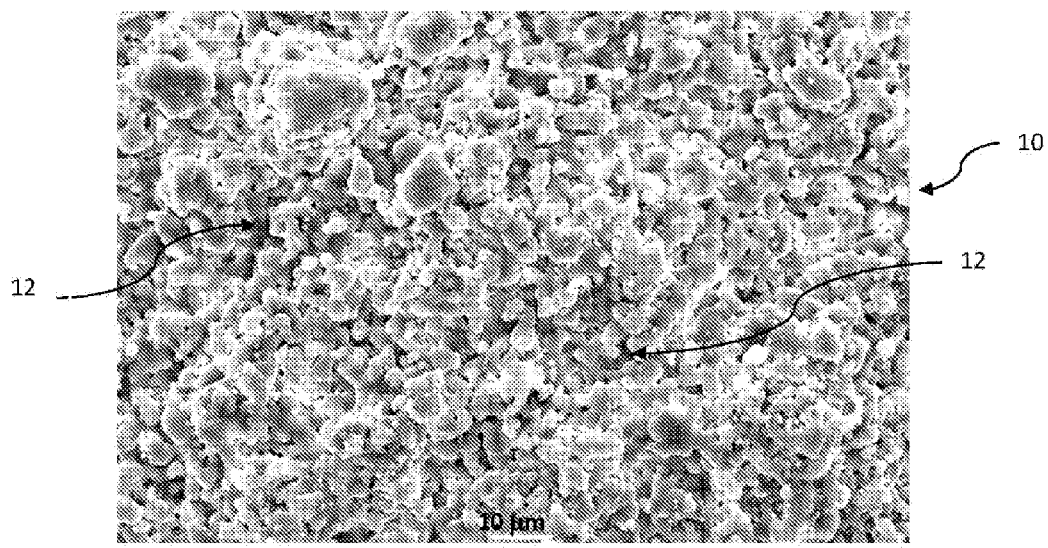
FIG. 2 illustrates an enlarged image obtained from the scanning electron microscope (SEM) of the granule of FIG. 1.

In the present document, the expression biomaterial is used to indicate a biocompatible material capable of being interfaced with a biological system with the aim of increasing, processing or replacing any tissue, organ or function of the system.

The present invention regards a method for providing a calcium phosphate-based biomaterial in form of re-absorbable granules 10 and/or aggregates 100 thereof.

Such method comprises the steps of providing at least one calcium phosphate-based ceramic powder and providing at least one aqueous solution comprising a natural polysaccharide. Such natural polysaccharide may be sodium alginate or chitosan or a mixture thereof and it is dissolved in the aqueous solution.

The method further comprises a step of preparing a ceramic suspension 30 obtained by mixing the ceramic powder in form of calcium phosphate in the aforementioned aqueous solution comprising a natural polysaccharide.

Such ceramic powder comprises calcium phosphate with a calcium on phosphorous ratio (Ca/P) comprised between 1 and 2, such as for example hydroxyapatite (HA) and/or calcium deficient hydroxyapatite (HACaD) and/or beta-tricalcium phosphate (β-TCP) and/or tetracalcium phosphate (TTCP) and/or alpha-tricalcium phosphate (α-TCP) and/or mixtures thereof.

Granules 10 and/or aggregates 100 thereof obtained starting from the ceramic suspension 30 described above, depending on the type of ceramic powder contained therein, may be chemically constituted by only one phase, such as for example granules 10 and/or aggregates 100 thereof constituted only by HA or (β-TCP), or by several phases comprised in the percentage range between 5 and 95%, such as for example granules 10 and/or aggregates 100 thereof constituted by HA and β-TCP in 60-40% composition. The possibility of mixing different ceramic powders within the same granule 10 (for example β-TCP and HA, etcetera) allows obtaining granules 10 with the desired biphasic chemical composition. Such biphasic chemical composition may be, in the final granule, different from the initial powder ratio, i.e. it may have a final ratio of the ceramic powders varied with respect to that provided initially, due to the processes the granule is subjected to, such as drying, washing and possible sintering.

Such ceramic powders have a granulometry comprised between 0.5 microns and 200 microns. The granulometry of the initial powder is important given that it allows modulating the internal microporosity and the consistency of the granule, as better described hereinafter. Generally, the greater the dimension of the powder, the greater the internal microporosity but the smaller the consistency of the granule.

The aqueous solution, to which the ceramic powder in form of calcium phosphate is added with the aim of obtaining the ceramic suspension 30, is an aqueous solution in which at least one natural polysaccharide is previously dissolved in percentage comprised between 0.1 and 5%.

Such natural polysaccharide may be, for example, sodium alginate or chitosan dissolved in an aqueous solution of acetic acid with a concentration comprised between 0.1 and 5%.

The concentration of the ceramic powder in form of calcium phosphate may vary between 1-200 g/l.

Sodium alginate, for example, is a chemical compound formed by the sodium salt of alginic acid; alginates, generally, are salts deriving from the cellular wall of brown algae from which alginic acid, a natural polymer of D-mannuronic acid and guluronic acid, is extracted, which can be converted into the sodium or calcium salt (alginate) thereof. The first, soluble in water, is used as a thickener and stabilizer in the food and pharmaceutical industry. The second, insoluble, is used in medicaments and in hemostatic gauzes.

Alginate is used for the rheological properties thereof suitable for the purpose and the capacity thereof to form a hydrogel relatively stable in various conditions.

Chitosan is a polysaccharide suitable for the purpose.

The aforementioned step of mixing the ceramic powder in form of calcium phosphate with the aqueous solution determines the obtainment of at least one homogeneous ceramic suspension 30.

The at least one ceramic suspension 30 thus obtained is passed and extruded through at least one nozzle 38, through the known technology referred to as "droplet extrusion."

In such method, the at least one ceramic suspension 30 is made to exit from the at least one nozzle 38, of dimensions comprised between 50 and 2000 microns, in at least one laminar flow 32, which is perturbed, through means 34 which determine a physical perturbation or through any other process suitable for the purpose, and fragmented into droplets 36. The frequency of perturbation is comprised between 100 and 150 Hz.

Droplets 36 of at least one ceramic suspension 30 fall and, thus, they are immersed in a cross-linking solution 40 having a pH comprised between 3 and 12; such cross-linking solution 40 comprising a catalyst and/or a polysaccharide at a concentration which may vary between 0.01 M and 3 M. Preferably, the pH values are comprised between 4.5 and 9 and/or the concentrations vary in the range between 0.01 M and 0.1 M.

Such catalyst may comprise zinc acetate and/or strontium chloride and/or a catalyst suitable for the purpose and/or a combination thereof.

Such polysaccharide may comprise a natural polysaccharide such as chitosan and/or the sodium alginate and/or a polysaccharide suitable for the purpose.

The cross-linking solution 40 may comprise calcium chloride and/or sodium tripolyphosphate in combination with the aforementioned catalyst and/or natural polysaccharide.

In a version of the invention, the cross-linking solution 40 used comprises strontium chloride and/or zinc acetate. The cross-linking of droplets 36 by using strontium chloride occurs by replacing sodium ions, specific of alginate, with strontium ions present in the solution. Given that the dimension of calcium ions and strontium ions ($Ca^{++}$ and $Sr^{++}$) is similar, the obtained porosity shall be similar to that obtained by cross-linking the granules 10 in a calcium chloride solution, but with the advantage of replacing the sodium ions of the alginate with the strontium ions of the solution, which, with respect to the calcium ions, have the best properties in terms of osteointegration in that they facilitate the formation of osteoblasts and reduce the activity of the osteoclasts. In case of use of a cross-linking solution 40 comprising zinc ions, they have a smaller ionic dimension with respect to strontium ions and calcium. Thus, also in this case a replacement of the sodium ions specific of the alginate occurs, but the cross-linking of the droplets 36 is slower, with the possibility of obtaining a porosity that is less distributed and with greater dimensions with respect to the previous case.

In other versions of the invention other solutions containing both zinc and strontium nitrates or sulfates can be used as cross-linking solutions 40.

In the cross-linking solution 40, droplets 36 of calcium phosphate and polysaccharide-based suspension 30 are consolidated and jellified assuming a conformation of particles 42. Such particles 42 may have one conformation, such as, for example, "droplet-like" or substantially spherical-shaped or different shapes and they can be even or uneven. Furthermore, the distribution of conformations of such particles 42 may be random. The two main mechanisms that occur in this step and which can also be simultaneous, are the ionotropic jellification, i.e. the ionic exchange between the natural polysaccharide present in the droplets 36 and the cross-linking solution 40 and the polyelectrolyte complexation, i.e. the combination of two polymers or salts with opposite valence, which also occurs between the polysaccharide present in the droplets 36 and the cross-linking solution 40. These two mechanisms allow the instantaneous formation of a gel and thus the formation of the granules 10.

In this phase it is essential to control the pH of the cross-linking solution 40. Actually, it influences the degree and the speed of jellification and, in addition, the final composition of the granule 10. A very acid pH, for example comprised between 1 and 5, indeed, may dissolve the calcium phosphate and thus increase the ions present in the cross-linking solution 40 and thus increase the efficiency of the gel cross-linking.

Particles 42 which are instantaneously formed in the cross-linking solution 40 remain and are left to harden therein over various periods of time comprised between 1 minute and 24 hours, for example about 30-45 minutes or a few hours. The dimensions of such particles 42 may be controlled by adjusting the extrusion flow speed, vibration frequency or by applying a coaxial airflow which limits the divergence of the flow from a vertical line. In such period, the completion of the jellification of the polysaccharide contained in the particles 42 starting from outside up to the internal thereof occurs.

Table 1 illustrates the various possible compositions of a cross-linking solution in case of granules 10 and/or aggregates 100 respectively obtained using a sodium alginate or chitosan aqueous solution.

TABLE 1

| Aqueous solution | Cross-linking agent | | | | | |
|---|---|---|---|---|---|---|
| | Calcium chloride | Zinc acetate | Strontium chloride | Sodium tripolyphosphate | Sodium alginate | Chitosan |
| Sodium alginate | x | x | | | | |
| | | x | | | | |
| | | x | x | | | |
| | x | | x | | | |
| | | | | | | x |
| | x | | | | | x |
| | | x | | | | x |
| | | | x | | | x |
| | | x | x | | | x |
| | x | | x | | | x |
| Chitosan | x | | | x | | |
| | | x | | x | | |
| | | | x | x | | |
| | | | | x | x | |
| | x | | | x | x | |
| | | x | | x | x | |
| | x | | x | x | | |
| | | x | x | x | | |

After the step of maintaining in the cross-linking solution 40 particles 42 not entirely consolidated are obtained, which are washed in water or any other liquid suitable for removing the excess material, such as for example the cross-linking solution 40. The control of the washing step is particularly important in the process given that it allows eliminating possible impurities which may generate foreign undesired phases in the composition of the final granule 10.

Such particles 42 are thus dried in an oven at 37° C. for 10-12 hours. In order to speed up the production process the drying may be carried out in a microwave oven at a temperature comprised between 30 and 60° C. for a range of time comprised between 1 and 2 hours.

During the drying step the liquid component contained in the particles 42 is eliminated. Such liquid component may be partly made up of the aqueous solution in which the ceramic powder is mixed, and/or partly the cross-linking solution 40 and/or partly the washing solution used in the very step of washing such particles 42.

The drying step is very important in case of production agglomerates 100 of granules 10. Actually, during drying should the granules 10 be suitably separated in a special container, manually or automatically and with the aim of avoiding contact therebetween, the production of single granules occurs; vice versa, should the moist granules 10 be left in contact, or more suitably should they be handled and compacted in an automated or manual manner with the aim of having aggregates, the formation of agglomerates 100 of dimensions greater or equal to 1000 microns occurs.

Granules 10 and/or agglomerates 100 have in this step a microporosity formed by pores 12 of micrometric dimensions. Such microporosity is created at the interface between ceramic powder and jellifying polysaccharide due to the presence of an inherent microporosity made of such material and given that the jellifying polysaccharide partly covers the outer surface of the particles constituting the ceramic powder.

The drying step may be followed by a further step in which granules 10 and/or agglomerates 100 of granules 10 are sintered at a temperature comprised in the range from 500° C. to 1500° C. over a period of time comprised between 1 and 6 hours.

The morphology of granules 10 after sintering is visible in FIGS. 1-4.

The sintering time and temperature are very important given that they allow obtaining the composition and the desired consistency also influencing microporosity.

Generally, also the dimension of the calcium phosphate powder influences the porosity of the granules 10 and/or agglomerates 100: indeed, the greater the dimension of the powder, the greater the internal microporosity, but smaller than the consistency of the granule. This occurs due to the fact that the neck that is formed in the sintering step between a particle of initial powder and the other shall be smaller.

Such sintering step determines the hardening and the consolidation of the material forming each granule 10 and/or agglomerate 100 and simultaneously, determines the burning, with ensuing elimination, of the organic material contained within each granule 10 and/or agglomerate 100 and which in the specific case is constituted by a gel of polysaccharides originating following the cross-linking of the polysaccharide of the ceramic suspension 30 within the cross-linking solution 40, such as for example alginate, chitosan or a combination of alginate-chitosan or chitosan-tripolyphosphate. The elimination of the polysaccharide gel allows obtaining, in granule 10, a microporosity formed by interconnected pores 12 and of micrometric dimensions comprised between 0.1 microns and 100 microns. Such microporosity—an enlargement which is visible in FIG. 2—due to the small dimensions of the pores 12 which constitute it can be substantially distributed over the entire volume of granule 10 and offer a greater specific surface.

The dimensions of the porosity, besides other parameters of the process, also depend on the granulometry of the calcium phosphate powders used initially: in particular using powders of a different granulometry allows different porosity values, with pores of different dimensions.

In a version of the invention, granules 10 and/or aggregates of granules 100 are inserted into the human organism immediately after the drying step and subsequent sterilising. Such sterilization step may be carried out through gamma rays, beta rays, ethylene oxide, autoclaves or other methods suitable for the purpose.

Thus, in such case the sintering step with ensuing elimination of the organic portion of the polysaccharide contained therein does not occur.

Such organic portion not eliminated by the sintering step stimulates the organic portion present in the bone, thus accelerating the bone regeneration process. The polysaccharide gel behaves as an amorphous of macro-molecules of glucidic origin in which the collagen fibres that form the connective tissue which covers and makes the bone flexible will be formed.

The porosity of granules 10 also depends on the cross-linking solution 40 which is used. Using different solutions, such as for example a solution of calcium chloride or zinc acetate, allows obtaining granules with different internal microporosity given that the involved ion, calcium ion or zinc ion in this example, has different dimensions in the ionotropic jellification.

Figure 3:
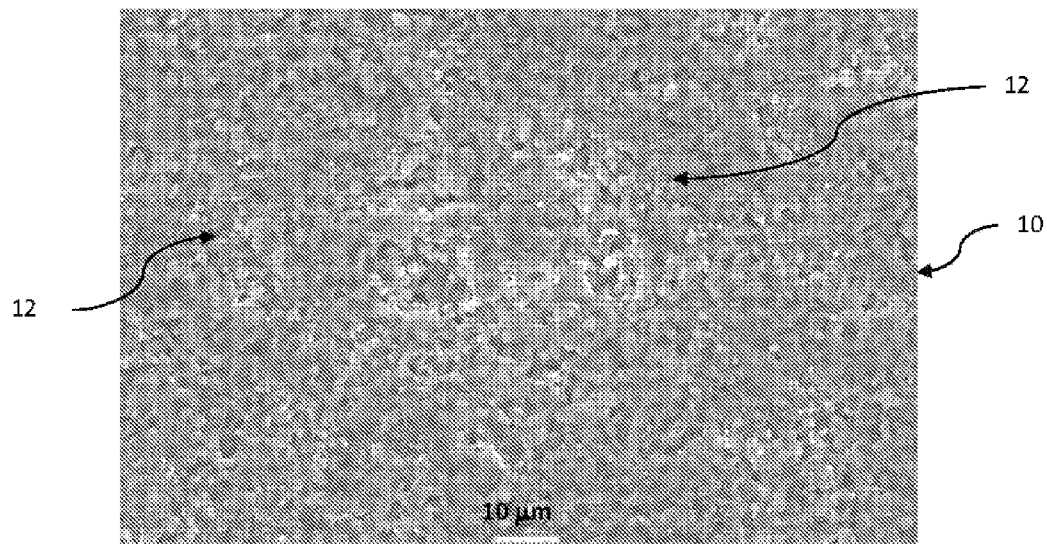
FIG. 3 illustrates an image obtained from the scanning electron microscope (SEM) of a version of a granule according to the present invention.
Figure 4:
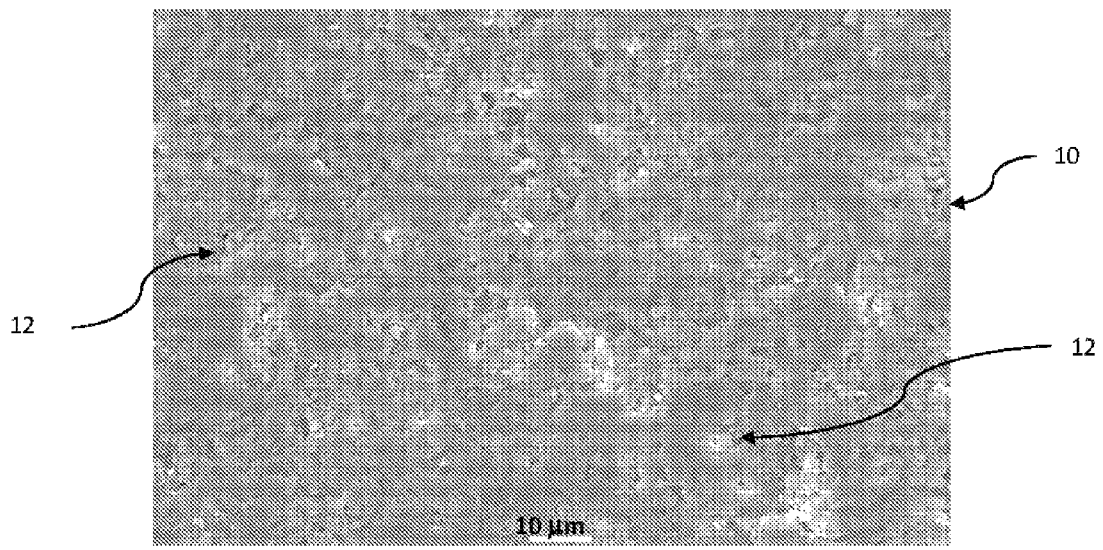
FIG. 4 illustrates an image obtained from the scanning electron microscope (SEM) of a further version of a granule according to the present invention.
Figure 5:
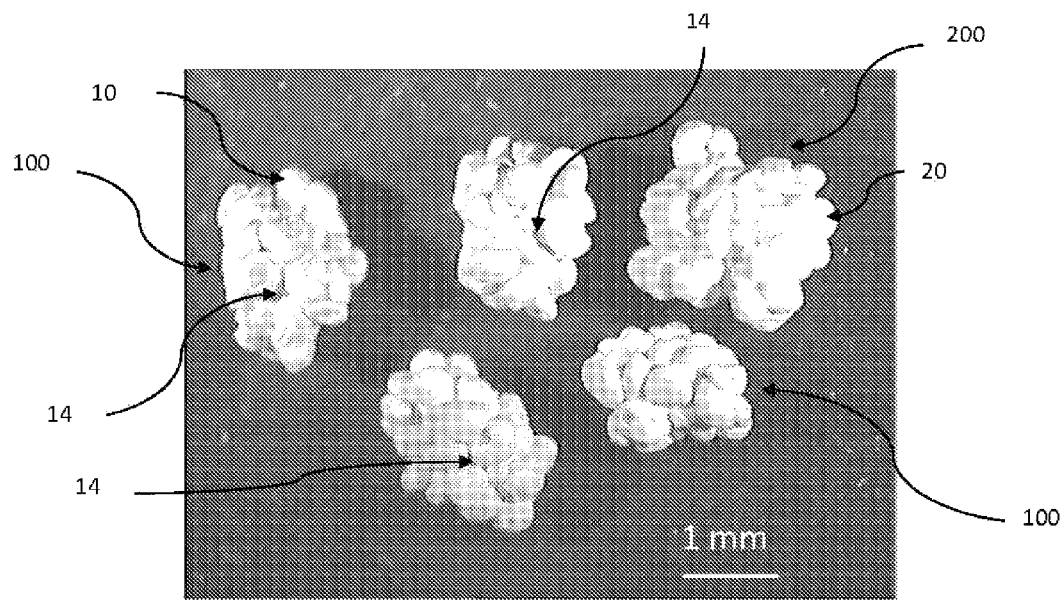
FIG. 5 illustrates an image obtained from the optical microscope of yet another version of granules according to the present invention in form of aggregates of granules.
Figure 6:
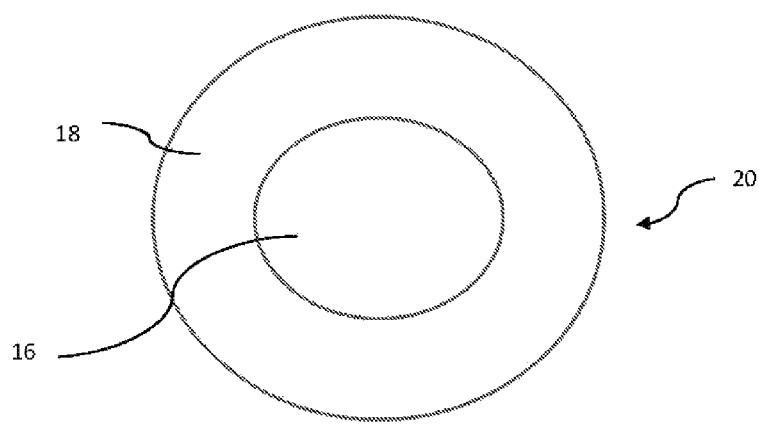
FIG. 6 illustrates a further version of a granule according to the present invention.
Figure 7:
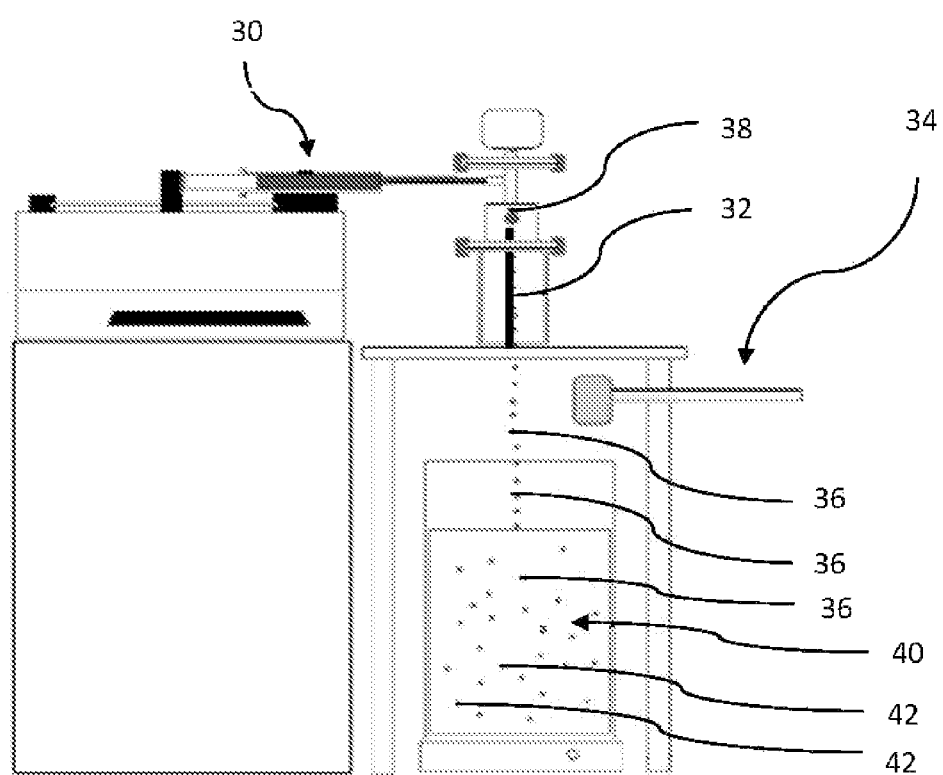
FIG. 7 illustrates a scheme of the device used for the method according to the present invention.

FIG. 4 shows the porosity of a granule 10 obtained by cross-linking in a calcium chloride solution, while FIG. 3 shows that of a granule 10 obtained in a zinc acetate solution.

In case of agglomerates of granules 100, after drying and/or sintering there will be both a macroporosity 14 between one granule and another and a microporosity interconnected on the single granule. Macroporosity 14 facilitates the vascularization of the granule and a better and quicker re-growth of the bone therein.

The possibility of producing agglomerates 100 is very important given that it allows optimally filling bone lacunae of large dimensions. Besides, the mechanical resistance of the agglomerate will be guaranteed by the presence of necks between one granule and another which were formed during the sintering step.

The method applied according to the present invention for obtaining granules 10 and/or aggregates of granules 100 is thus very simple, inexpensive and practical.

The sterilization step described above may be possibly carried out after the sintering step.

In the version in which the natural polysaccharide used for the initial aqueous solution is sodium alginate, another factor which influences both the porosity 12 and the jellification of the granules 10 is the type of alginate used and, in particular, the guluronic acid/mannuronic acid ratio (G/M) present therein. If the ratio G/M is greater than 1, the instantaneous jellification is facilitated given that guluronic acid has a more complex and branched polymeric chain with respect to mannuronic acid. A jellification thus produced requires a greater cross-linking of the gel and thus a microporosity 12 of greater dimensions, but less uniformly distributed within the granule 10.

In addition, during such step of possible sintering the aggregation of the ceramic particles that compose the granules occurs. Thus it is possible to confer uniform dimensions and shapes thereto. Such characteristic confers an easier migration of the bone tissue therein.

The chemical compositions of granules thus obtained depend on the types of calcium phosphate powders used for preparing the initial ceramic suspension 30. In particular, such compositions can be formed by one or more calcium phosphates with a Ca/P ratio comprised between 1 and 2.

An advantage of the method according to the present invention lies in the simplicity thereof, both as regards the components used and the steps for obtaining granules and/or agglomerates. Organic solvents or oils are absent, thus allowing recovering the particles constituting granules without requiring performing further washing steps.

In addition, the method according to a version of the invention comprises a step of adding the so-called "doping" substances, separately or combined, such as, for example, zinc, strontium, etcetera, and/or mixtures thereof, so as to confer improved osteoconductive properties to granules.

In a version of the invention, the at least one doping ion is determined by the presence, in the cross-linking solution 40, of a catalyst containing the at least one ion with which one intends to dope the composition of granule 10.

Such doping occurs during the consolidation and the jellification of granules 10 or agglomerates of granules 10 through the catalyst contained in the cross-linking solution 40.

An example of a catalyst is zinc acetate and/or strontium chloride. In such case, the catalyst present in the cross-linking solution 40 has both cross-linking and doping function at the same time. Furthermore, thus the catalyst is uniformly distributed within the granules 10 given that it is trapped in the interconnected matrix of the gel which involves the entire granule. Furthermore, the catalyst well distributed within the granule 10 has the function of replacing calcium in the present crystalline structures and thus stabilising a phase with respect to another one allowing the production of different chemical compositions by varying the type and concentration of the ion. Thus, the catalyst, besides serving as a cross-linking agent, also serves as a stabilizer of given crystalline phases present. For example, zinc stabilizes the β-TCP phase with respect to HA in biphasic products and, thus, varying the concentration of the zinc ion allows varying the HA/β-TCP ratio with respect to the reticulated granules with solutions containing calcium ion alone, such as for example calcium chloride, or not containing any ion, such as for example chitosan, in which this possibility is not present.

The doping substances are obtained by controlling the molar concentration of the cross-linking solution 40 containing the aforementioned catalyst. Thus, the doping step is inherent in the method, without requiring providing for a specific step of adding such substances.

Another method for adding the doping agents is that of adding composites, such as for example magnesium oxide (MgO) and/or zinc oxide (ZnO), to the ceramic initial powder of calcium phosphate.

Thus this allows obtaining doped granules and/or agglomerates of granules.

The role of the doping agents is very important for the improvement of osteointegration of the bone substitute and the regeneration of the bone. It is important to control the chemical composition of the doped granule so as to avoid excessive concentrations of doping agents, which could be toxic for the organism (for example, a percentage of ZnO greater than 1.5% in weight).

The granules of biocompatible material can be used in injectable form and, in this case, the fluidity properties thereof during the injection are more predictable due to the shape and the regular dimensions of such particles. In order to facilitate the injectability, granules 10 and/or aggregates 100 thereof can also be added with other organic and inorganic biomaterials, for example with gels of various types, with the aim of facilitating the filling bone defects and guaranteeing a greater stability of granules 10 and/or agglomerates 100 upon inserting in the lacunae.

The method, according to a further version of the invention, provides for the possibility of producing biphasic granules 20 and/or aggregates 200 thereof constituted by a central nucleus of a first material 16 and an outer shell in a second material 18. Granules 20 and/or aggregates 200 thereof may also comprise several steps and be constituted by a central nucleus of a first material 16 and at least one outer shell in a second material 18.

For the production of granules 20 of this type at least two ceramic suspensions 30 made of different material are prepared, in which both the powders and the solutions in which they are dispersed can be differentiated. Generally, for the objects provided for, calcium phosphate-based ceramic powders are used, with a different calcium on phosphorous ratio (Ca/P) ratio, such as for example HA and β-TCP, dispersed in aqueous solutions with natural polysaccharides, such as for example sodium alginate or chitosan or mixtures thereof. The at least two suspensions thus prepared are extruded in a composite laminar flow formed by an internal laminar flow of the first ceramic solution of the first material 16, which is, partly or totally covered by at least one laminar flow of at least one second ceramic suspension formed by at least one second material 18, obtaining droplets 36 comprising a central nucleus formed by the first calcium phosphate-based material 16 and at least one outer shell formed by the at least one second calcium phosphate-based material 18. The second material 18 may have a calcium on phosphorous ratio different from that of the first material 16.

Such extrusion may for example be obtained through at least one coaxial nozzle capable of allowing encapsulating a suspension, which will constitute the central nucleus 16, within the other, which will constitute the outer shell 18.

The composite laminar flow is perturbed, as indicated previously, and the droplets 36 thus obtained are immersed in a cross-linking solution 40, for example constituted by tripolyphosphate or by the other substances listed above.

When the composite laminar flow is fragmented into droplets 36 concentric particles made up of the at least two different materials are formed, in which the first material 16 is internal and the at least one second material 18 constitutes at least one outer shell surrounding the nucleus made up of the first material 16. Such formation occurs due to the different viscosity and surface tension of the at least two ceramic suspensions 30 involved.

In an example of such embodiment, the materials which constitute the central nucleus 16 and the outer shell 18 may be two calcium phosphates with different speed of re-absorption, leading to a biomaterial which modulates the re-growth of the bone over time.

The same operating method can be used for inserting controlled release drugs within the granules exploiting the inherent microporosity thereof.

In such case, the extrusion step occurs by extruding a suspension of a drug or medicament and at least one ceramic suspension 30 in a composite laminar flow formed by the internal laminar flow of the drug and/or medicament suspension, which is covered by at least one laminar flow of at least one ceramic suspension 30, obtaining droplets 36 comprising a central nucleus formed by the drug and/or medicament and at least one outer shell formed by the at least one ceramic suspension 30. Such extrusion may occur, for example, through a coaxial nozzle.

The drug and/or medicament comprises antibiotics, anti-inflammatories, anti-tumour drugs, analgesics and/or mixtures thereof.

The drug and/or medicament may comprise, additionally or alternatively with respect to the substances indicated above, mesenchymal stem cells, osteoblasts, growth factors, proteins, and/or combinations thereof.

Granules and/or aggregates thereof, according to the present invention, may thus be used for releasing drugs or other substances, such as bone fillers, for sealing prosthesis etcetera.

Thus substantially coaxial granules and/or agglomerates of granules are obtained.

The present invention further refers to a calcium phosphate-based biomaterial in form of granules 10, 20 and/or agglomerates 100, 200 of re-absorbable dried granules comprising at least one calcium phosphate-based ceramic powder and a natural jellified polysaccharide, in which granules 10, 20 comprise a microporosity formed by pores 12 of micrometric dimensions and/or in which agglomerates 100, 200 further comprise a macroporosity 14 between one granule and another, obtainable according to the method described above.

In a version, the present invention further refers to a calcium phosphate-based biomaterial in form of granules 10, 20 and/or agglomerates 100, 200 of re-absorbable granules sintered comprising at least one calcium phosphate-based ceramic powder, in which granules 10, 20 comprise a microporosity formed by interconnected pores 12, of micrometric dimensions comprised between 0.1 microns and 100 microns, uniformly and substantially distributed over the entire volume of granules 10, 20, and/or in which agglomerates 100, 200 further comprise a macroporosity 14 between one granule and another, obtainable according to the method described above.

The jellified polysaccharide is obtained by cross-linking the polysaccharide, present in a ceramic suspension 30, with a catalyst and/or a natural polysaccharide, contained in a cross-linking solution 40, as described previously.

Granules 10, 20 and/or agglomerates 100, 200 are granules 10, 20 and/or agglomerates 100, 200 hardened by means of sintering.

Granules 10, 20 and/or agglomerates 100, 200 comprise at least one doping substance such as strontium ions and/or zinc ions and/or magnesium and/or mixtures thereof, etcetera, for increasing the osteointegration thereof.

Granules 10, 20 and/or agglomerates 100, 200 comprise a central nucleus formed by a first calcium phosphate-based material 16 and at least one outer shell formed by at least one second calcium phosphate-based material 18, in which the second material 18 may have a calcium on phosphorous ratio different from that of the first material 16.

Granules 10, 20 and/or agglomerates 100, 200 comprise a central nucleus formed by a first drug and/or medicament-based material 16 and at least one outer shell formed by at least one second calcium phosphate-based material 18.
Granules 10, 20 and/or agglomerates 100, 200 comprise calcium phosphate with a calcium on phosphorous ratio (Ca/P) comprised between 1 and 2, such as for example hydroxyapatite (HA) and/or calcium deficient hydroxyapatite (HACaD) and/or beta-tricalcium phosphate (β-TCP) and/or tetracalcium phosphate (TTCP) and/or alpha-tricalcium phosphate (α-TCP) and/or mixtures thereof, thus determining granules 10, 20 and/or agglomerates 100, 200 chemically constituted by only one type of powder or by several types of powder comprised in the percentage range from 5 to 95%.

Granules 10, 20 have dimensions comprised between 10 and 2000 microns.

It has thus been observed how the invention attains the proposed objectives.

The present invention was described according to preferred embodiments but equivalent variants may be conceived without departing from the scope of protection outlined by the following claims.

Furthermore, some of the characteristics described for a variant of the present invention may be combined with characteristics described for a different variant, without departing from the scope of protection of the present invention.

The invention claimed is:

1. A method of making a biomaterial in a form of at least one of granules and agglomerates of granules comprising the following steps:
    preparing an aqueous solution comprising a natural polysaccharide and water;
    adding at least one ceramic powder comprising calcium phosphate to said aqueous solution comprising a natural polysaccharide, mixing said at least one ceramic powder comprising calcium phosphate and said aqueous solution comprising a natural polysaccharide selected among sodium alginate and chitosan and mixtures thereof for preparing at least one ceramic suspension;
    extruding said at least one ceramic suspension in at least one laminar flow;
    fragmenting said at least one laminar flow of said at least one ceramic suspension into droplets and obtaining said droplets formed by said at least one ceramic suspension;
    preparing a cross-linking solution comprising a catalyst and a natural polysaccharide of the cross-linking solution; wherein said natural polysaccharide of the cross-linking solution is selected among sodium alginate and chitosan; and wherein said catalyst is selected among zinc acetate, strontium chloride and a combination thereof;
    controlling the pH of the cross-linking solution to have a pH comprised between 1 and 5;
    submerging by dropping said droplets of said at least one ceramic suspension in the cross-linking solution comprising the catalyst and the natural polysaccharide of the cross-linking solution;
    wherein said submerging step comprises immersing said droplets of said at least one ceramic suspension in said cross-linking solution wherein said catalyst serves as an agent for doping said granules;
    maintaining said droplets in said cross-linking solution for a time comprised between 30-45 minutes;
    consolidating and jellifying said droplets with said cross-linking solution for obtaining a jellified polysaccharide comprising a conformation of particles;
    washing said particles in a liquid suitable for eliminating the excess of material and impurities; and
    drying said particles with manual or automated separation of said particles so as to avoid contact therebetween, for obtaining at least said granules, and further comprising compacting said particles for obtaining said agglomerates of granules,
    wherein in said drying step a microporosity is formed made up by pores of micrometric dimensions.

2. The method according to claim 1, wherein said cross-linking solution comprises at least one of calcium chloride and sodium tripolyphosphate in combination with said at least one of the catalyst and said natural polysaccharide of said cross-linking solution.

3. The method according to claim 1, wherein said extrusion step occurs by extruding at least two ceramic suspensions with different calcium to phosphate ratio in a composite laminar flow formed by an internal laminar flow of a first ceramic suspension of a first calcium-phosphate-based material which is covered by at least one laminar flow of at least one second ceramic suspension formed by at least one second calcium phosphate-based material, and obtaining droplets comprising a central nucleus formed by said first material and at least one outer shell formed by said at least one second material.

4. The method according to claim 1, wherein said step of preparing an aqueous solution comprises dissolving a polysaccharide selected from the group consisting of sodium alginate, chitosan and mixtures thereof in said aqueous solution at a concentration comprised between 0.1 and 5%.

5. The method according to claim 1, wherein after the step of drying further comprising a step of sintering at least one of said granules and said agglomerates, wherein said sintering step comprises: elimination, by means of burning, of said jellified polysaccharide, hardening and consolidation of said granules and/or agglomerates, and formation of at least one of a microporosity formed by interconnected pores substantially distributed over the entire volume of said granules and a macroporosity formed between one granule and another of said agglomerates, wherein said sintering step occurs at a temperature comprised between 500° C. and 1500° C. over a period of time comprised between 1 and 6 hours, and wherein said microporosity is of micrometric dimensions comprised between 0.1 microns and 100 microns.

6. The method according to claim 1, wherein after the step of drying, further comprising a sterilization step selected from the group consisting of gamma rays, beta rays, ethylene oxide and autoclaves.

7. The method according to claim 1, wherein said step of submerging said droplets occurs in said cross-linking solution having a pH comprised between 3 and 5 and wherein said step of immersing said droplets occurs in said cross-linking solution having a concentration of the catalyst comprised between 0.01 and 3 M.

8. The method according to claim 1, wherein said step of preparing at least one ceramic suspension includes selecting calcium phosphate with a calcium to phosphorous ratio (Ca/P) comprised between 1 and 2 from the group consisting of hydroxyapatite (HA), calcium deficient hydroxyapatite (HACaD), beta-tricalcium phosphate (β-TCP), tetracalcium phosphate (TTCP), alpha-tricalcium phosphate (α-TCP) and mixtures thereof, thus forming at least one of said granules and agglomerates chemically constituted by only one type of said ceramic powder or by several types of said ceramic powder comprised between 5 and 95%, wherein said ceramic powder has a granulometry comprised between 0.5 microns and 200 microns.

9. The method according to claim 1, wherein said step of preparing at least one ceramic suspension occurs by dispersing in said aqueous solution said ceramic powder at a concentration comprised between 1 and 200 g/l.

10. A method of making a biomaterial in a form of at least one of granules and agglomerates of granules comprising the following steps:
preparing an aqueous solution comprising a natural polysaccharide and water;
adding at least one ceramic powder comprising calcium phosphate to said aqueous solution comprising a natural polysaccharide, mixing said at least one ceramic powder comprising calcium phosphate and said aqueous solution comprising a natural polysaccharide selected among sodium alginate and chitosan and mixtures thereof for preparing at least one ceramic suspension;
extruding said at least one ceramic suspension in at least one laminar flow, wherein said extruding step consists of extruding at least two ceramic suspensions with different calcium to phosphate ratio or a drug suspension and at least one ceramic suspension in a composite laminar flow formed by an internal laminar flow of a first ceramic suspension of a first calcium phosphate-based material or said drug suspension, which is covered by at least one laminar flow of at least one second ceramic suspension formed by at least one second calcium phosphate-based material or at least one ceramic suspension, obtaining droplets comprising a central nucleus formed by said first material or by said drug suspension and at least one outer shell formed by said at least one second material or by said at least one ceramic suspension;
fragmenting said at least one laminar flow of said at least one ceramic suspension into droplets and obtaining said droplets formed by said at least one ceramic suspension;
preparing a cross-linking solution comprising a catalyst and a natural polysaccharide of the cross-linking solution; wherein said natural polysaccharide of the cross-linking solution is selected among sodium alginate and chitosan; and wherein said catalyst is selected among zinc acetate, strontium chloride and a combination thereof;
controlling the pH of the cross-linking solution to have a pH comprised between 1 and 5;
submerging by dropping said droplets of said at least one ceramic suspension in a cross-linking solution comprising the catalyst and the natural polysaccharide of the cross-linking solution;
maintaining said droplets in said cross-linking solution for a time comprising between 30-45 minutes;
consolidating and jellifying said droplets with said cross-linking solution for obtaining a jellified polysaccharide comprising a conformation of particles;
washing said particles in a liquid suitable for eliminating the excess of material and impurities; and
drying said particles with manual or automated separation of said particles so as to avoid contact therebetween, for obtaining said granules, and further comprising compacting said particles for obtaining said agglomerates of granules, wherein in said drying step a microporosity is formed made up by pores of micrometric dimensions.

11. The method according to claim 10, wherein said step of preparing at least one aqueous solution comprising a natural polysaccharide includes dissolving a polysaccharide selected from the group consisting of sodium alginate, chitosan and mixtures thereof in said aqueous solution wherein said drug suspension is selected from the group consisting of antibiotics, anti-inflammatories, anti-tumour drugs, analgesics, mesenchymal stem cells, osteoblasts, growth factors, proteins and mixtures thereof.

12. The method according to claim 10, wherein after the step of drying further comprising a step of sintering at least one of said granules and said agglomerates, wherein said sintering step comprises: elimination, by means of burning, of said jellified polysaccharide, hardening and consolidation of said granules and/or agglomerates, and formation of at least one of a microporosity formed by interconnected pores substantially distributed over the entire volume of said granules and a macroporosity formed between one granule and another of said agglomerates, wherein said sintering step occurs at a temperature comprised between 500° C. and 1500° C. over a period of time comprised between 1 and 6 hours, and wherein said microporosity is of micrometric dimensions comprised between 0.1 microns and 100 microns.

13. The method according to claim 10, wherein prior to the step of submerging, further comprising a step of adding at least one of a doping substance, a catalyst, strontium ions, zinc ions and mixtures thereof, in said cross-linking solution and wherein after the step of drying, further comprising a sterilization step selected from the group consisting of gamma rays, beta rays, ethylene oxide and autoclaves.

14. The method according to claim 10, wherein said step of preparing at least one ceramic suspension includes selecting calcium phosphate with a calcium to phosphorous ratio (Ca/P) comprised between 1 and 2 from the group consisting of hydroxyapatite (HA), calcium deficient hydroxyapatite (HACaD), beta-tricalcium phosphate (β-TCP), tetracalcium phosphate (TTCP), alpha-tricalcium phosphate (α-TCP) and mixtures thereof, thus forming at least one of said granules and agglomerates chemically constituted by only one type of said ceramic powder or by several types of said ceramic powder comprised between 5-95%, wherein said step of providing said ceramic powder occurs by selecting a ceramic powder having a granulometry comprised between 0.5 microns and 200 microns.

15. The method according to claim 10, wherein said step of preparing an aqueous solution includes dissolving in said aqueous solution said natural polysaccharide in a percentage comprised between 0.1 and 5% and wherein said step of preparing at least one ceramic suspension occurs by dispersing in said aqueous solution said ceramic powder at a concentration comprised between 1 and 200 g/l.

16. The method according to claim 1, wherein said step of submerging said droplets occurs in said cross-linking solution having a pH comprised between 4.5 and 5.

17. The method according to claim 1, wherein said step of submerging said droplets occurs in said cross-linking solution having a concentration of the catalyst comprised between 0.01 and 0.1 M.

18. The method according to claim 1, wherein said step of preparing said aqueous solution comprises dissolving chitosan said aqueous solution at a concentration comprised between 0.1 and 5% and further comprising adding acetic acid.

19. The method according to claim 1, wherein said extrusion step occurs by extruding a drug suspension and at least one ceramic suspension in a composite laminar flow formed by an internal laminar flow of said drug suspension, which is covered by at least one laminar flow of at least one ceramic suspension, and further comprising obtaining droplets comprising a central nucleus formed by said drug suspension and at least one outer shell formed by said at least one ceramic suspension, wherein said drug suspension is selected from the group consisting of antibiotics, anti-inflammatories, anti-tumour drugs, analgesics, mesenchymal stem cells, osteoblasts, growth factors, proteins and mixtures thereof.

20. The method according to claim 10, wherein said step of submerging said droplets occurs in said cross-linking solution having a pH comprised between 3 and 5.

21. The method according to claim 10, wherein said step of submerging said droplets occurs in said cross-linking solution having a concentration of the catalyst comprised between 0.01 and 3 M.

22. The method according to claim 10, wherein said cross-linking solution comprises at least one of calcium chloride and sodium tripolyphosphate in combination with said at least one of a catalyst and said natural polysaccharide of said cross-linking solution.

23. The method according to claim 10, wherein said step of preparing said aqueous solution comprises dissolving chitosan in said aqueous solution at a concentration comprised between 0.1 and 5% and further comprising adding acetic acid.

24. The method according to claim 10, wherein said drug suspension is selected from the group consisting of antibiotics, anti-inflammatories, anti-tumour drugs, analgesics, mesenchymal stem cells, osteoblasts, growth factors, proteins and mixtures thereof.

25. The method of claim 1, wherein following the drying step, further comprising compacting said particles, for obtaining said agglomerates of granules, wherein a macroporosity is formed between one granule and another of said agglomerates.

26. A method of making a biomaterial in a form of at least one of granules and agglomerates of granules comprising the following steps:
preparing an aqueous solution comprising a natural polysaccharide and water;
adding at least one ceramic powder comprising calcium phosphate to said aqueous solution comprising a natural polysaccharide, mixing said at least one ceramic powder comprising calcium phosphate and said aqueous solution comprising a natural polysaccharide selected among sodium alginate and chitosan for preparing at least one ceramic suspension;
extruding said at least one ceramic suspension in at least one laminar flow;
fragmenting said at least one laminar flow of said at least one ceramic suspension into droplets and obtaining said droplets formed by said at least one ceramic suspension;
preparing a cross-linking solution comprising a catalyst and a natural polysaccharide of the cross-linking solution; wherein said natural polysaccharide of the cross-linking solution is selected among sodium alginate and chitosan; and wherein said catalyst is selected among zinc acetate, strontium chloride and a combination thereof;
controlling the pH of the cross-linking solution to have a pH comprised between 1 and 5;
submerging by dropping said droplets of said at least one ceramic suspension in a cross-linking solution comprising the catalyst and the natural polysaccharide of the cross-linking solution, wherein said submerging step comprises immersing said droplets of said at least one ceramic suspension in said cross-linking solution comprising at least one of the catalyst and the natural polysaccharide of the cross-linking solution, wherein during said consolidation and jellification of said natural polysaccharide contained in said ceramic suspension, said at least one of granules and said agglomerates of granules are doped through said catalyst of said cross-linking solution, said catalyst serving as an agent for doping said at least one of granules and said agglomerates of granules;
maintaining said droplets in said cross-linking solution for a time comprising between 1 minute and 24 hours for providing consolidation and jellification of said droplets with said cross-linking solution for obtaining a jellified polysaccharide comprising a conformation of particles;
washing said particles in a liquid suitable for eliminating the excess of material and impurities; and
drying said particles with manual or automated separation of said particles so as to avoid contact therebetween, for obtaining said granules, and with automated or manual compaction of said particles, for obtaining said agglomerates of granules, wherein in said drying step at least one of a microporosity is formed made up by pores of micrometric dimensions and a macroporosity is formed between one granule and another of said agglomerates,
and further comprising a step of sintering at least one of said granules and said agglomerates, wherein said sintering step comprises: elimination, by means of burning, of said jellified polysaccharide, hardening and consolidation of said granules and/or agglomerates, and formation of at least one of a microporosity formed by interconnected pores substantially distributed over the entire volume of said granules and a macroporosity formed between one granule and another of said agglomerates, wherein said sintering step occurs at a temperature comprised between 500° C. and 1500° C. over a period of time comprised between 1 and 6 hours, and wherein said microporosity is of micrometric dimensions comprised between 0.1 microns and 100 microns.

* * * * *